United States Patent

Draper

(10) Patent No.: US 6,509,472 B2
(45) Date of Patent: Jan. 21, 2003

(54) 4-CYCLOHEXYL-1,3,2-OXAZABOROLIDINE CHIRAL ACCESSORIES

(75) Inventor: Richard W. Draper, North Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/943,127

(22) Filed: Aug. 30, 2001

(65) Prior Publication Data

US 2002/0038053 A1 Mar. 28, 2002

Related U.S. Application Data

(60) Provisional application No. 60/231,630, filed on Sep. 11, 2000.

(51) Int. Cl.$^7$ .................. C07D 231/00; C07F 5/04; C07C 29/143; C07C 211/03
(52) U.S. Cl. ............... 548/110; 558/289; 564/455; 568/881
(58) Field of Search ............. 558/289; 564/455; 568/881; 548/110

(56) References Cited

U.S. PATENT DOCUMENTS

| | | | | |
|---|---|---|---|---|
| 4,943,635 A | * | 7/1990 | Corey | 546/13 |
| 5,552,548 A | * | 9/1996 | Quallich | 546/13 |
| 5,852,221 A | * | 12/1998 | Kashihara et al. | 568/814 |
| 6,005,133 A | * | 12/1999 | Quallich | 558/289 |
| 6,037,505 A | * | 3/2000 | Quallich | 568/881 |

FOREIGN PATENT DOCUMENTS

| WO | WO 93/23408 | 11/1993 |
|---|---|---|
| WO | WO 94/26751 | 11/1994 |

OTHER PUBLICATIONS

The Second International Symposium on Technologies for the Production of Enantiomerically Pure Chemicals, (Mar. 14–17, 1995).

Prasad K., et al., An Optimised in situ Procedure for the Oxazaborolidine Catalysed Enantioselective Reduction of Prochiral Ketones, *Tetrahedron: Asymmetry*, vol. 7, No. 11, pp. 3147–3152, (1996).

Masui M. et al, A Practical Method for Asymmentric Borane Reduction of Prochiral Ketones Using Chiral Amino Alcohols and Trimethyl Borate, (Mar. 1997).

Wallbaum, S., et al., Asymmetric Syntheses with Chiral Oxazaborolidnes, *Tetrahedron: Asymmetry* vol. 3, No. 12, pp. 1475–1504, (1992).

Shen Z., et al., Chiral oxazaborolidines bearing a 1—of 2 naphthylmethyl group as catalysts for the enantioselective borane reduction of ketones: experimental and quantum chemical calculations, *Tetrahedron Asymmetry* 9 pp. 1091–1095, (1998).

Stone, G., Oxazaborolidine Catalytzed Borane Reductions of Ketones: A Significant Effect of Temperature on Selectivity., *Tetrahedron: Asymmetry* vol. 5., No. 3. pp. 465–472, (1994).

Berenguer R. et al., Enantioselective Reduction of Ketones Catalysed by 1,3,2–Oxazaborolidines Prepared from Phenylglycine. *Tetrahedron: Asymmetry* vol. 5., No. 2., pp. 165–168, (1994).

* cited by examiner

*Primary Examiner*—Deborah C. Lambkin
(74) *Attorney, Agent, or Firm*—Allan N. Kutzenco; Palaiyur S. Kalyanaraman

(57) ABSTRACT

Prochiral ketones are enantioselectively reduced to chiral secondary alcohols with a compound having the formula I:

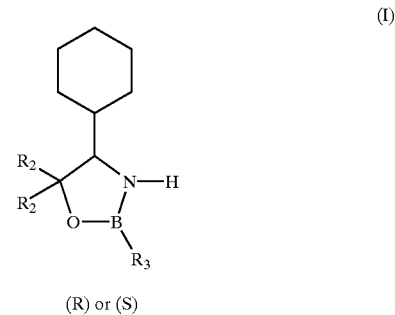

(R) or (S)

where, the two $R_2$ groups are identical and are each a substituted or unsubstituted, aryl, alkyl, cycloalkyl or aralkyl group; and $R_3$ is a hydrogen atom or a substituted or unsubstituted, alkyl, aryl, aralkyl or alkoxy group; wherein the substituents on the $R_2$ and $R_3$ groups are substantially non-reactive.

19 Claims, No Drawings

4-CYCLOHEXYL-1,3,2-OXAZABOROLIDINE CHIRAL ACCESSORIES

CROSS-REFERENCE TO RELATED APPLICATIONS

This application claims the benefit of U.S. Provisional Application Serial No. 60/231,630, filed Sep. 11, 2000.

BACKGROUND OF THE INVENTION

1. Field of the Invention

The invention relates to novel 4-cyclohexyl substituted 1,3,2-oxazaborolidine chiral accessories of (R) and (S) configurations and processes for producing and using them. More particularly, the present invention relates to a process for an enantioselective reduction of prochiral ketones to chiral secondary alcohols using the novel chiral accesories.

2. Description of Related Art

Chiral accessories of formula A, which are useful for catalyzing an enantioselective reduction of ketones by borane, are well known in the art. See e.g., Tetrahedron: Asymmetry, Vol. 5, No. 2, pp. 165–168 (1994); Tetrahedron: Asymmetry, Vol. 5, No. 3, pp. 465–472 (1994); Tetrahedron: Asymmetry, Vol. 9, No. 7, pp. 1091–1095 (1998); Tetrahedron: Asymmetry Report Number 13, Vol 3, No. 12, pp. 1475–1504 (1992); Tetrahedron: Asymmetry, Vol. 7, No. 11, pp. 3147–3152 (1996); and SynLett, pp. 273–274 (March, 1997).

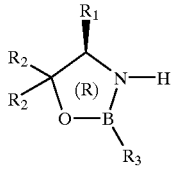

(A)

where, $R_1$ is an alkyl or aryl group, $R_2$ is an alkyl or aryl group, $R_3$ is a hydrogen atom or an alkyl, aryl, aralkyl or alkoxy group.

These chiral accessories are generally prepared from enantiomerically pure amino acids. Consequently, only compounds having absolute (S) configurations can generally be prepared inexpensively, since only (S)-amino acids are typically found in nature. In contrast, (R)-amino acids are usually relatively expensive, because they are generally not found in nature and must be prepared either de novo, which entails separation from racemic mixtures, or by expensive enantioselective routes.

Many useful pharmaceutical agents require for their manufacture, chiral secondary alcohol intermediates having an absolute configuration which is introduced by means of the chiral accessories of type A having the (R) absolute configuration. It is obviously a disadvantage that expensive (R)-amino acids are required for the manufacture of many useful pharmaceutical agents. One of the few inexpensive (R)-amino acids is (R)-phenylglycine (formula 1), which is a precursor to (R)-4-phenyl-5,5-disubstituted oxazaborolidines of formula B. (R)-phenylglycine is relatively cheap because it is manufactured on a multi-ton scale as an intermediate in the synthesis of penicillin G. However, (R)-4-phenyl-5,5-disubstituted oxazaborolidines of formula B that are derived

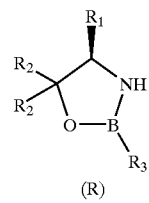

(R)

$R_1$ = alkyl or aryl;
$R_2$ = alkyl or aryl; and
$R_3$ = H, alkyl, aryl or alkoxy.

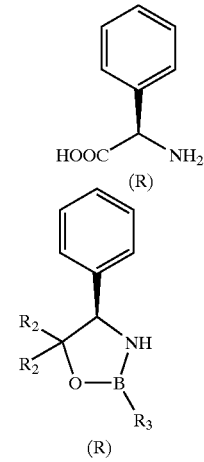

$R_2$ = alkyl or aryl; and
$R_3$ = H, alkyl, aryl or alkoxy.

from (R)-phenylglycine are often not especially efficient chiral accessories, as they can lead to lower enantiomeric ratios in the borane reduction products of prochiral ketones.

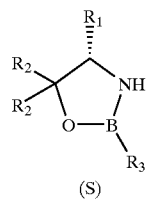

(S)

$R_1$ = alkyl or aryl;
$R_2$ = alkyl or aryl; and
$R_3$ = H, alkyl, aryl or alkoxy.

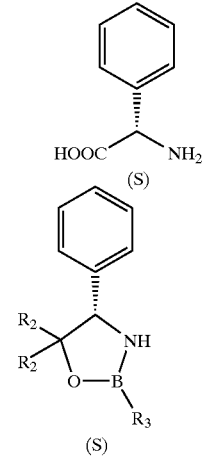

$R_2$ = alkyl or aryl; and
$R_3$ = H, alkyl, aryl or alkoxy.

Common compounds of formulas A and A' have the $R_1$ substituent equal to an isopropyl or —$(CH_2)_3$— group, with the terminal methylene moeity connected to the adjacent nitrogen atom on the ring (replacing a hydrogen atom) forming a five-membered ring. Unfortunately, the known compounds in the (R) configuration with $R_1$ equal to, respectively, the isopropyl or —$(CH_2)_3$— group, are not inexpensive since they are derived from, respectively, (R)-valine and (R)-proline, which are relatively expensive synthetic amino acids. Prior attempts to produce quality, inexpensive chiral accessories of formula A with (R) or (S) configurations have only met with minimal success.

A goal achieved by this invention was to overcome these and other prior art problems. Accordingly, this invention, which includes novel, quality, inexpensive chiral accessories of the (R) or (S) absolute configurations, provides a superior benefit over the current art.

It is an object of this invention to provide inexpensive, novel chiral accessories of the (R) and (S) absolute configurations.

It is a further object of this invention to provide a process for producing inexpensive, novel chiral accessories of the (R) and (S) absolute configurations.

It is yet another object of this invention to reduce prochiral ketones enantioselectively to chiral secondary alcohols with inexpensive, novel chiral accessories of the (R) and (S) absolute configurations.

These and other objects of the present invention will become apparent after reading the following description and claims.

DEFINITIONS AND USAGE OF TERMS

The term "enantioselective catalyst," as used herein, means a compound which together with a borane reagent reduces a prochiral ketone to an optically active alcohol.

The term "chiral accessory," as used herein, is synomous with the term "enantioselective catalyst."

The term "prochiral ketone," as used herein, means a ketone which on reduction can produce an optically active alcohol. Furthermore, a prochiral ketone will have structurally different moieties attached to its carbonyl group.

The term "alkyl," as used herein, means an unsubstituted or substituted, straight or branched, hydrocarbon chain. "Lower alkyl" has from 1 to 8 carbon atoms, preferably, from 1 to 4 carbon atoms.

The term "cycloalkyl," as used herein, means an unsubstituted or substituted, saturated carbocyclic ring. "Lower cycloalkyl" has from 3 to 8 carbons.

The term "aryl," as used herein, means a substituted or unsubstituted aromatic carbocyclic ring. Preferred aryl groups include phenyl, tolyl, xylyl, cumenyl and napthyl.

The term "aralkyl," as used herein, means an alkyl moiety substituted with an aryl group. Preferred aralkyls include benzyl, phenylethyl, and 1- and 2-naphthylmethyl.

The term "alkoxy," as used herein, means a straight or branched, hydrocarbon chain attached to an oxygen atom which is bonded to another atom of a compound. "Lower alkoxy" has from 1 to 8 carbon atoms, preferably, from 1 to 4 carbon atoms.

The terms "secondary chiral alcohol" and "optically active alcohol," as used herein, each mean an alcohol compound having a hydroxyl group attached to a carbon atom bearing a hydrogen atom and two other non-identical groups.

The term "substantially non-reactive substituent," as used herein, means a substituent that is not materially affected by either the reagents or solvents used during a chiral borane reduction of a ketone. That is, no significant side reactions occur involving the substituents, which would materially impair the optical and chemical efficacies of the compounds or processes at issue.

The term "enantiomeric excess" (ee), as used herein, means the excess amount of one enantiomer over the other enantiomer in a mixture of enantiomers, expressed in terms of percent, for example, a 9:1 ratio of R:S is equal to an 80% enantiomeric excess (ee) of (R).

The term "borane reagent," as used herein, means a reagent that is a source of borane or supplies borane in a reaction. Typical reagents which are sources of borane include diborane gas ($H_3B$—$BH_3$), borane-THF complex (in THF solution), borane dimethylsulfide complex and borane 1,4-oxathiane complex.

It is understood by those skilled in the art that the chiral accessories described herein exist in both the (R) and (S) absolute configurations. A (S) configuration refers to a counterclockwise arrangement of high to low priority substituents about an asymmetric carbon atom. A (R) configuration refers to a clockwise arrangement of high to low priority substituents about an asymmetric carbon atom. Compounds having (R) absolute configurations are specifically described herein. However, it is known to those skilled in the art that (S) configurations can also be produced from appropriately configured starting materials. The compounds described and claimed herein include their enantiomers, and solvates and salts thereof.

It is also known to a skilled artisan that the substituents defined in the compounds of the invention may themselves be substituted with a variety of groups, such as alkyl, cycloalkyl, aryl, aralkyl, hydroxy and alkoxy groups, or a variety of atoms, such as halogen atoms. These groups and atoms are substantially non-reactive substituents.

SUMMARY OF THE INVENTION

The invention relates to a compound having the formula I:

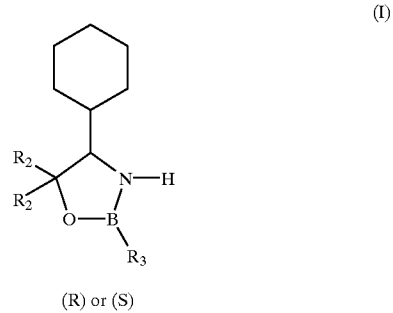

(R) or (S)

where, the two $R_2$ groups are identical and=substituted or unsubstituted, aryl, alkyl, cycloalkyl or aralkyl, and $R_3$=H or substituted or unsubstituted, aryl, alkyl, aralkyl or alkoxy, for example, an alkoxy group, $OR_5$, where $R_5$ is a substituted or unsubstituted 20 alkyl group, and wherein the substituents on the $R_2$ and $R_3$ groups are substantially non-reactive.

This compound is useful as a chiral accessory.

The present invention also relates to a compound having the formula II:

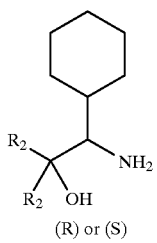

(II)

(R) or (S)

where, the $R_2$ groups are defined the same as above for the compound of formula I, and wherein the substituents are substantially non-reactive.

The compounds of formula II are precursors that are useful for the preparation of the compounds of formula I. The invention further relates to a process for producing a compound having the formula I or II. The process comprises:

(a) reacting a (R or S)-cyclohexylglycine ester hydrochloride or hydrobromide compound having the formula III:

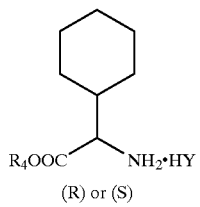

(III)

(R) or (S)

where, $R_4$=alkyl and Y=Cl or Br, with an organometallic reagent having the formula $R_2MgX$ or $R_2Li$, where, $R_2$ is defined the same as above for the compound of formula I and X is Cl, Br or I, to form the compound of formula II, and (b) reacting the compound of formula II formed in step (a) with (i) $BH_3$, (ii) $(BOR_3)_3$ or $R_3B(OH)_2$ or (iii) $B(OR_5)_3$, respectively, where, $R_3$ and $R_5$ are defined the same as above for the compound of formula I, to form the compound of formula I, where, respectively, $R_3$=(i) H, (ii) alkyl, aryl or aralkyl or (iii) $OR_5$.

Furthermore, the present invention relates to a process for asymmetrically reducing prochiral ketones to secondary chiral alcohols, comprising reacting a prochiral ketone compound having the formula IV:

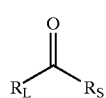

(IV)

where, $R_L$ and $R_S$ are non-identical, unsubstituted or substituted, aryl, alkyl, aralkyl or heteroaryl groups, with borane derived from a borane reagent, in the presence of a chiral accessory compound having the formula I according to the invention described above.

DESCRIPTION OF PREFERRED EMBODIMENTS

The compounds of the invention are represented herein without their absolute chiral configuration ((R) or (S)) or in the (R) configuration. The invention further encompasses compounds of the (S) configuration, as those skilled in the art know, for example, that compounds of formula I can exist in either the (R) or (S) absolute configuration, depending on the absolute configuration(s) of the starting material(s) from which they are prepared (e.g., compounds of formula II and III).

In the compounds of formula I, the two $R_2$ groups are identical, preferably, substituted or unsubstituted, aryl or aralkyl, such as arylmethyls, more preferably, substituted or unsubstituted, phenyl, benzyl, 1-naphthylmethyl, 2-naphthylmethyl, 1-naphthyl or 2-naphthyl, and most preferably, substituted or unsubstituted phenyl. Furthermore, in the compounds of formula I, $R_3$ is, preferably, a hydrogen atom or a substituted or unsubstituted, alkyl, aryl, such as a phenyl group, aralkyl or alkoxy group, and more preferably, a hydrogen atom or a substituted or unsubstituted, lower alkyl (e.g., 1–8 carbon atoms) or lower alkoxy (e.g., 1–8 carbon atoms) group. Most preferably, $R_3$ is a hydrogen atom or a methoxy, methyl or butyl group.

Representative formula I compounds are illustrated below:

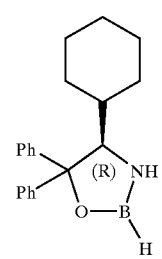

I.1: (R)-4-cyclohexyl-5,5-diphenyl-1,3,2-oxazaborolidine;

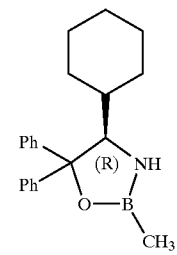

I.2: (R)-4-cyclohexyl-5,5-diphenyl-2-methyl-1,3,2-oxazaborolidine;

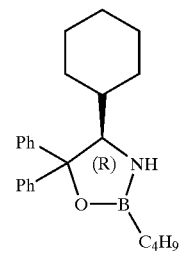

I.3: (R)-2-butyl-4-cyclohexyl-5,5-diphenyl-1,3,2-oxazaborolidine;

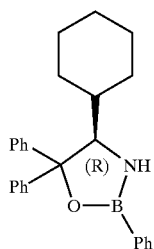

I.4: (R)-4-cyclohexyl-2,5,5-triphenyl-1,3,2-oxazaborolidine;

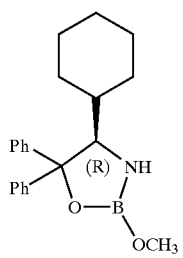

I.5: (R)-4-cyclohexyl-5,5-diphenyl-2-methoxy-1,3,2-oxazaborolidine;

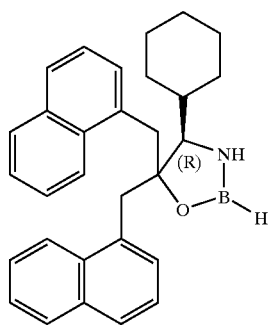

I.6: (R)-4-cyclohexyl-5,5-di(1-naphthylmethyl)-1,3,2-oxazaborolidine;

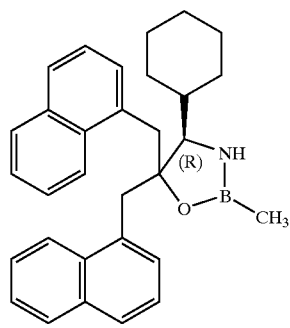

I.7: (R)-4-cyclohexyl-5,5-di(1-naphthylmethyl)-2-methyl-1,3,2-oxazaborolidine;

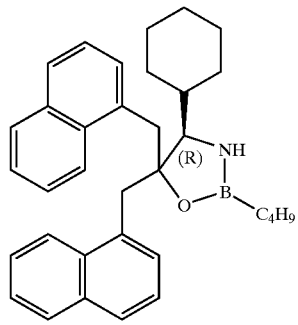

I.8: (R)-4-cyclohexyl-5,5-di(1-naphthylmethyl)-2-butyl-1,3,2-oxazaborolidine;

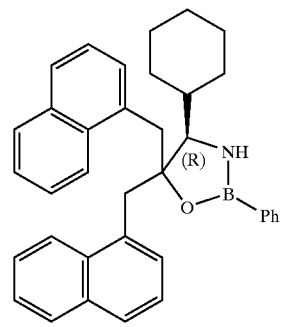

I.9: (R)-4-cyclohexyl-5,5-di(1-naphthylmethyl)-2-phenyl-1,3,2-oxazaborolidine;

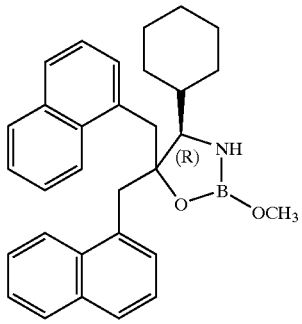

I.10: (R)-4-cyclohexyl-5,5-di(1-naphthylmethyl)-2-methoxy-1,3,2-oxazaborolidine;

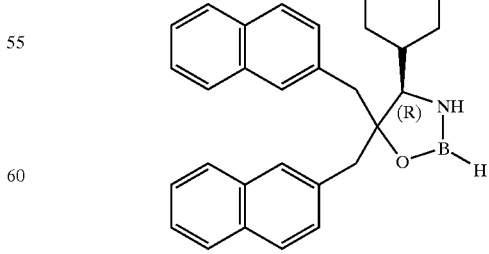

I11: (R)-4-cyclohexyl-5,5-di(2-naphthylmethyl)-1,3,2-oxazaborolidine;

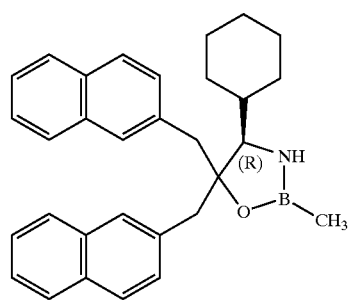

I.12: (R)-4-cyclohexyl-5,5-di(2-naphthylmethyl)-2-methyl-1,3,2-oxazaborolidine;

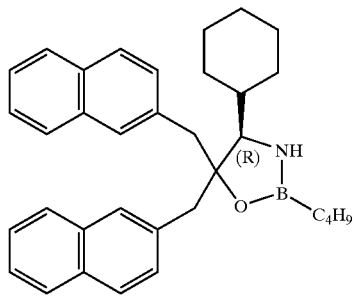

I.13: (R)-4-cyclohexyl-5,5-di(2-naphthylmethyl)-2-butyl-1,3,2-oxazaborolidine;

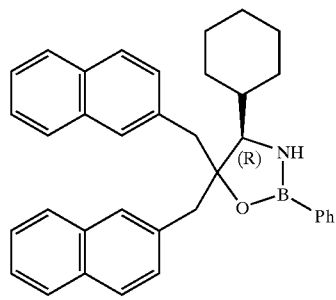

I.14: (R)-4-cyclohexyl-5,5-di(2-naphthylmethyl)-2-phenyl-1,3,2-oxazaborolidine;

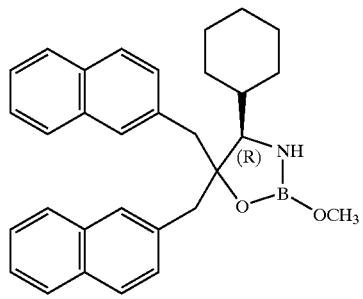

I.15: (R)-4-cyclohexyl-5,5-di(2-naphthylmethyl)-2-methoxy-1,3,2-oxazaborolidine;

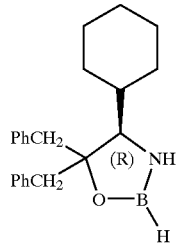

I.16: (R)-4-cyclohexyl-5,5-dibenzyl-1,3,2-oxazaborolidine;

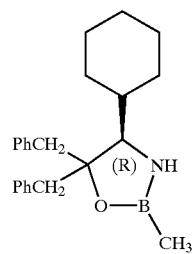

I.17: (R)-4-cyclohexyl-5,5-dibenzyl-2-methyl-1,3,2-oxazaborolidine;

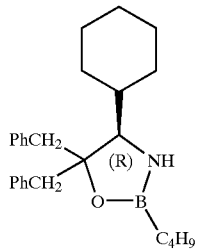

I.18: (R)-4-cyclohexyl-5,5-dibenzyl-2-butyl-1,3,2-oxazaborolidine;

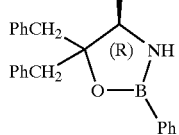

I.19: (R)-4-cyclohexyl-5,5-dibenzyl-2-phenyl-1,3,2-oxazaborolidine;

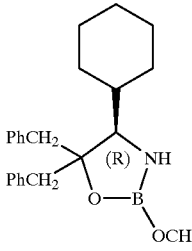

I.20: (R)-4-cyclohexyl-5,5-dibenzyl-2-methoxy-1,3,2-oxazaborolidine;

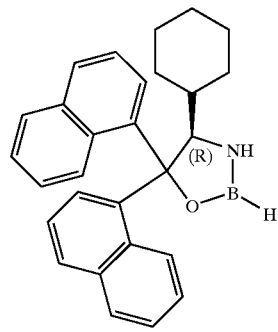

I.21: (R)-4-cyclohexyl-5,5-di(1-naphthyl)-1,3,2-oxazaborolidine;

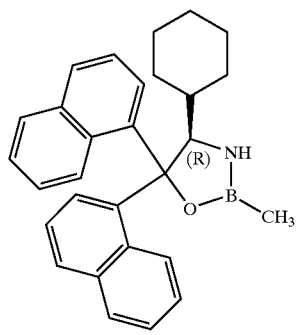

I.22: (R)-4-cyclohexyl-5,5-di(1-naphthyl)-2-methyl-1,3,2-oxazaborolidine;

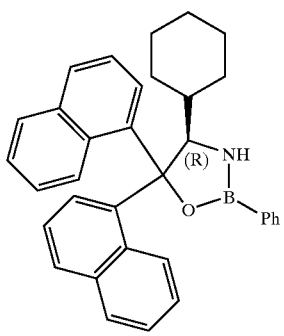

I.23: (R)-4-cyclohexyl-5,5-di(1-naphthyl)-2-phenyl-1,3,2-oxazaborolidine;

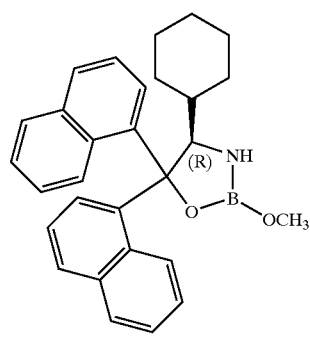

I.24. (R)-4-cyclohexyl-5,5-di(1-naphthyl)-2-methoxy-1,3,2-oxazaborolidine;

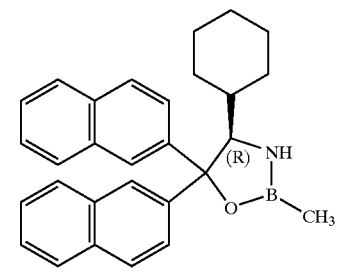

I.25: (R)-4-cyclohexyl-5,5-di(2-naphthyl)-1,3,2-oxazaborolidine;

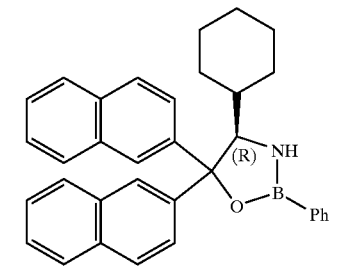

I.26: (R)-4-cyclohexyl-5,5-di(1-naphthyl)-2-methyl-1,3,2-oxazaborolidine;

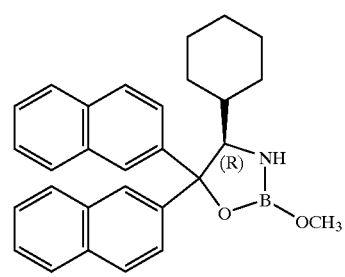

I.27: (R)-4-cyclohexyl-5,5-di(2-naphthyl)-2-phenyl-1,3,2-oxazaborolidine; and

I.28: (R)-4-cyclohexyl-5,5-di(2-naphthyl)-2-methoxy-1,3,2-oxazaborolidine.

The invention further includes the corresponding (S) enantiomers for the above depicted compounds of formula I. Likewise, the compounds having the formula II according to the invention are also represented herein in the (R) configuration, though it is understood by those skilled in the art that compounds of formula II, like with the compounds of formula I, can exist in the (S) configuration as well, depending on the configuration(s) of the starting material(s) from which they are prepared.

Like in the compounds of formula I, the two $R_2$ groups in the compounds of formula II are identical, preferably, substituted or unsubstituted, aryl or aralkyl, for example, arylmethyl, more preferably, substituted or unsubstituted, phenyl, benzyl, 1-naphthylmethyl, 2-naphthylmethyl, 1-naphthyl or 2-naphthyl groups. Most preferably, the two $R_2$ groups are substituted or unsubstituted phenyl groups.

Representative formula II compounds are illustrated below:

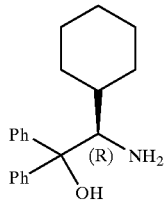

II.1: (R)-2-amino-2-cyclohexyl-1,1-diphenylethanol;

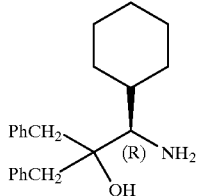

II.2: (R)-2-amino-1,1-dibenzyl-2-cyclohexylethanol;

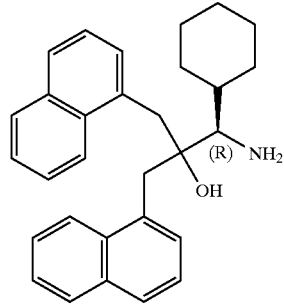

II.3: (R)-2-amino-2-cyclohexyl-1,1-di(1-naphthylmethyl) ethanol;

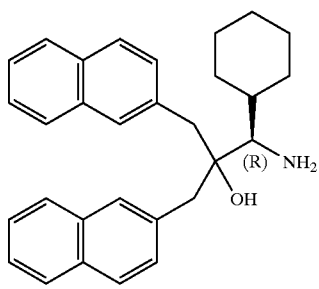

II.4: (R)-2-amino-2-cyclohexyl-1,1-di(2-naphthylmethyl) ethanol;

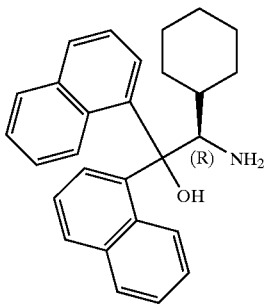

II.5: (R)-2-amino-2-cyclohexyl-1,1-di(1-naphthyl) ethanol; and

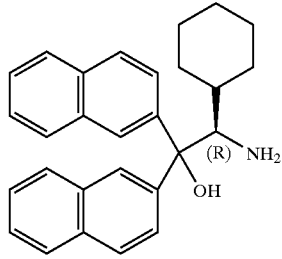

II.6: (R)-2-amino-2-cyclohexyl-1,1-di(2-naphthyl) ethanol.

The corresponding (S) enantiomers for the above depicted compounds of formula II are also encompassed by the invention.

A (R or S)-cyclohexylglycine ester hydrochloride or hydrobromide compound having the formula III may be used in the inventive process for producing a compound having the formula I. In step (a) of the inventive process, the reaction scheme advantageously proceeds as follows:

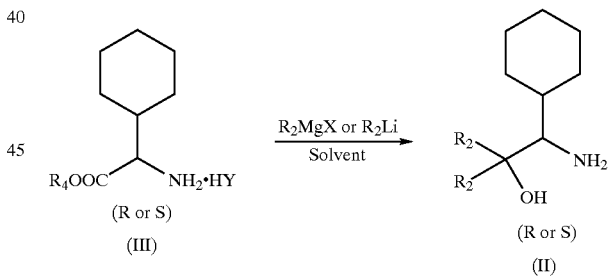

where, $R_4$=alkyl, preferably, lower alkyl (e.g., 1 to 8 carbon atoms); Y=Cl or Br; X=Cl, Br or I; and the $R_2$ groups are identical and=substituted or unsubstituted, aryl, alkyl, cycloalkyl or aralkyl An excess of a suitable organometallic reagent, $R_2MgX$ or $R_2Li$ (as a solution in an inert solvent), preferably, from about 3 to 6 equivalents, most preferably, about 6 equivalents, is added, advantageously, under nitrogen, to a solution or suspension of the (R or S)-cyclohexylglycine ester hydrochloride or hydrobromide compound having the formula III in an inert solvent, preferably, a dry inert solvent. The preferred organometallic reagents are organomagnesium (Grignard) and organolithium reagents. The organometallic reagents ($R_2MgX$ or $R_2Li$) useful in the inventive process are well-known in the art and are often commercially available or may be prepared from alkyl, cycloalkyl, aryl or aralkyl halides and by methods known in the art.

The preferred inert (i.e., non-reactive) solvents include tetrahydrofuran, diethyl ether, t-butylmethylether, dimethoxyethane, diethoxymethane, toluene, hexane, heptane, methylene chloride and mixtures thereof. The most preferred inert solvents are tetrahydrofuran, diethyl ether or a mixture of toluene and tetrahydrofuran. The reaction temperature is, preferably, from about −20° C. to reflux, more preferably, from about −10 to +45° C., and most preferably, from about 0 to +45° C. The reaction is advantageously run until it is complete, which generally takes less than 24 hours, and is quenched by adding dilute aqueous acid. By-product metal salts can form and may be separated off by, for example, filtration or extraction. The product compound-containing mixture is advantageously in an alkaline state prior to recovery of the product. Preferably, the pH is adjusted to about 9 or higher and the product compound of formula II may be isolated and purified by techniques well-known to those skilled in the art, such as extraction, chromatography, crystallization, sublimation and the like.

In step (b) of the process described above to produce compounds of formula I, the reaction scheme advantageously proceeds through three different ways ((i), (ii) or (iii)), depending on the structure of the boron-containing reagent. First, for (i) BH$_3$, the reaction scheme may proceed as follows:

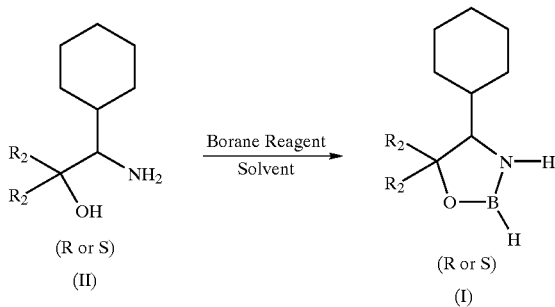

where, R$_2$ is defined the same as above and the borane reagent results in R$_3$=H.

For compounds of formula I, where R$_3$ is a hydrogen atom, a solution of a compound of formula II in an inert solvent, preferably, a dry inert solvent, is reacted, advantageously, under nitrogen, with a reagent that provides a source of borane. Reagents which are sources of borane include diborane gas (H$_3$B—BH$_3$), borane-tetrahydrofuran complex (in tetrahydrofuran solution), borane dimethylsulfide complex and borane 1,4-oxathiane complex. The preferred inert solvents include ethers, hydrocarbons and chlorinated hydrocarbons. The more preferred inert solvents include toluene, methylene chloride, tetrahydrofuran, diethyl ether, diethoxymethane and t-butylmethylether. The most preferred inert solvent is tetrahydrofuran. The preferred reaction temperature is from about −20 to +40° C. The more preferred reaction temperature is from about −20° C. to room temperature. The reaction is usually complete in less that 2 hours. Compounds of formula I, where R$_3$ is a hydrogen atom, are usually not isolated and are, preferably, generated and used in a solution to effect the chiral reduction of a prochiral ketone.

Second, for (ii) (BOR$_3$)$_3$ or R$_3$B(OH)$_2$ in step (b) of the process described above to produce compounds of formula I, where R$_3$ is an alkyl, aryl or aralkyl group, the reaction advantageously takes place accordingly to the following scheme:

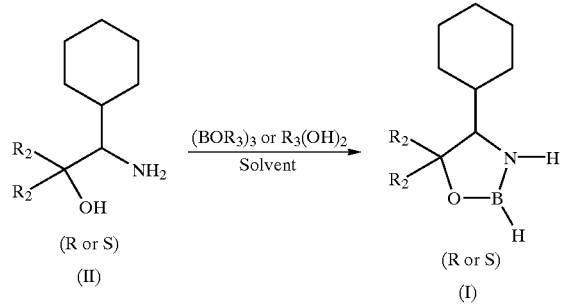

where, R$_2$ is defined the same as above and R$_3$=substituted or unsubstituted, alkyl, aryl or aralkyl.

For compounds of formula I, where R$_3$ is an alkyl, aryl or aralkyl group, a solution of a compound of formula II in a inert solvent, preferably, a dry inert solvent, is reacted, advantageously, under nitrogen, with a trialkyl or triaryl boroxine or an alkyl or aryl boric acid. The solvent is, advantageously, distilled out and fresh dry solvent is added until the reaction is complete. The compound of formula I, where R$_3$ is an alkyl, aryl or aralkyl group, may be isolated by removing all of the remaining solvent (e.g., by distillation) and purified by methods well-known in the art, such as distillation, crystallization and chromatography. The preferred inert solvents include ethers, such as tetrahydrofuran, and aromatic hydrocarbons, such as benzene, toluene and xylene. The more preferred inert solvents are tetrahydrofuran and toluene. The preferred reagents include trimethylboroxine, tri-n-butylboroxine, triphenylboroxine, methylboronic acid, butylboronic acid and phenylboronic acid. Most preferably, trimethyl boroxine, tri-n-butylboroxine and phenylboronic acid are used as the reagents. The compounds of formula I, where R$_3$ is an alkyl, aryl or aralkyl group, need not be isolated, but may be prepared in a solution which is used in the chiral borane reduction of prochiral ketones.

Third, for (iii) B(OR$_5$)$_3$ in step (b) of the process described above to produce compounds of formula I, where R$_3$ is, advantageously, substituted or unsubstituted alkoxy, for example, OR$_5$, where R$_5$ is an unsubstituted alkyl group, the reaction advantageously takes place accordingly to the following scheme:

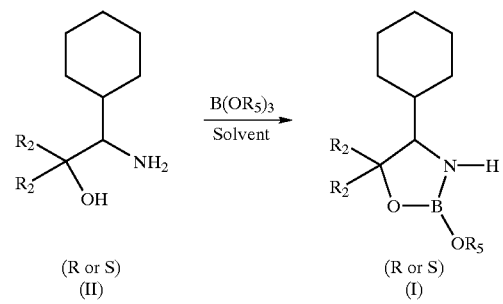

where, R$_2$ is defined the same as above and R$_3$=substituted or unsubstituted alkoxy, OR$_5$, where R$_5$ is a substituted or unsubstituted alkyl group.

For compounds of formula I, where R$_3$ is an alkoxy group, a solution of a compound of formula II in a inert solvent, preferably, a dry inert solvent, is reacted, advantageously, under nitrogen, with a trialkyl borate. The solvent is distilled out and fresh dry solvent is added until the reaction is complete. The compound of formula I, where R$_3$ is an alkoxy group, can be isolated by removing all of the remaining solvent by distillation and purified by methods well-known in the art, such as distillation, crystallization and chromatography. The preferred inert solvents are the same as defined above for where $R_3$ is an alkyl, aryl or aralkyl group. The preferred reagents include trimethylborate and tri-n-butylborate. The compounds of formula I, where $R_3$ is an alkoxy group, need not be isolated, but may be prepared in a solution which is used in the chiral borane reduction of prochiral ketones. The substituents on the R groups are substantially non-reactive.

The reaction for the asymmetric borane reduction of a prochiral ketone to a secondary chiral alcohol in the presence of a compound of formula I advantageously takes place accordingly to the following scheme:

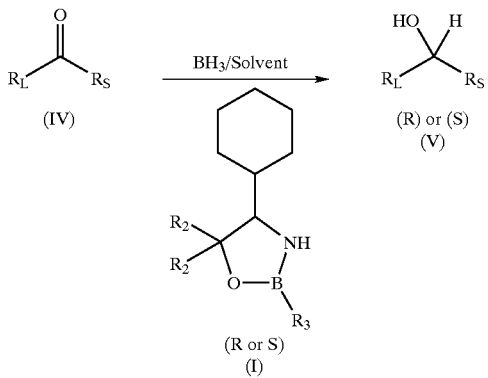

where, $R_L$ and $R_S$ are non-identical, unsubstituted or substituted, aryl, alkyl, aralkyl or heteroaryl groups; and $R_2$ and $R_3$ are defined the same as above formula I.

Moreover, in the inventive process for the asymmetric reduction of prochiral ketones to secondary chiral alcohols, $R_L$ is, preferably, a substituted or unsubstituted aryl group and $R_S$ is, preferably, a substituted or unsubstituted alkyl group, especially a halogenated alkyl group, such as $CF_3$, $CCl_3$, $CH_2Br$ or $CH_2Cl$. More preferably, $R_L$ is a substituted or unsubstituted phenyl group, such as $CF_3$-phenyl, and $R_S$ is $CH_2Br$, $CH_2Cl$ or $CH_2OCH_3$.

Compounds of formula I are relatively unstable. Therefore, for optimum efficiency it is preferable, but not mandatory, to generate these materials in an inert solvent, such as tetrahydrofuran, under nitrogen, and under anhydrous conditions, from a compound of formula II and the appropriate (i) borane reagent, (ii) substituted boroxine or boric acid or (iii) borate, as is described above. The reaction may be accomplished without isolation of the compound of formula I. Thus, for compounds of formula I, where $R_3$ is a (i) hydrogen atom, (ii) an alkyl, aryl or aralkyl group or (iii) an alkoxy group, a solution of a compound of formula II in an inert solvent is reacted with either (i) borane derived from a borane reagent, (ii) $(BOR_3)_3$ or $R_3B(OH)_2$ or (iii) $B(OR_5)_3$, respectively. Reagents that are sources of borane include, diborane gas ($H_3B$—$BH_3$), borane-THF complex (in THF solution), borane-dimethylsulfide complex and borane 1,4-oxathiane complex. The preferred inert solvents include ethers, hydrocarbons and chlorinated hydrocarbons. The more preferred inert solvents include, tetrahydrofuran, diethyl ether, diethoxymethane, t-butylmethylether, toluene, xylene and methylene chloride The most preferred solvents are THF and toluene.

The subject reaction to form compounds of formula I in solution advantageously takes place with about 1 equivalent of the boron containing reagents. The preferred reaction temperature is from about −20 to +40° C. The more preferred reaction temperature is from about −20° C. to +20° C. In cases where reagents of the type $(BOR_3)_3$, $R_3B(OH)_2$ or $B(OR_5)_3$ are used, distillation of the solvent may be required to complete the formation of the compound of formula I. The reaction is usually complete in less that 12 hours. After in-situ formation of the compound of formula I, where $R_3$ is a hydrogen atom or a substituted or unsubstituted, alkyl, aryl, aralkyl or alkoxy group, a borane reagent is added, followed by an addition of a prochiral ketone, which may be added neat or as a solution in an inert solvent, either gradually or all at once. The reaction is usually carried out at a temperature of from about −40 to +50° C., preferably, from about −20 to +50° C., and most preferably, from about 0 to +45° C.

A molar ratio of the compound of formula I to the prochiral ketone compound is, advantageously, from about 1:200 to 3:1. The optimum molar ratio of the compound of formula I to the prochiral ketone compound depends on the substrate, especially in cases where the prochiral ketone compound contains substituent groups that can complex with borane. The molar ratio of the prochiral ketone compound to the borane reagent is, preferably, from about 1:0.3 to 1:6. The precise reaction reagents and conditions (including the structure of the chiral catalyst compound of formula I and the reaction temperature, ratios of reagents and types of solvent(s) used) selected to achieve optimum enantioselectivity in the reduction of the prochiral ketone will depend on the structures of the $R_L$ and $R_S$ groups of the ketone of formula IV. When reduction of the ketone is substantially complete, usually in less than 2 hours, the chiral secondary alcohol product may be isolated by quenching the reaction with dilute aqueous acid and extracting the product into an organic solvent. The compound of formula II usually can be isolated from the aqueous phase, purified and reused. The chiral secondary alcohol product may be isolated from the organic phase and purified by techniques well-known to those skilled in the art, such as extraction, chromatography, distillation, crystallization and the like.

The general reaction pathways for producing the compounds of the invention in the (R) configuration are illustrated below:

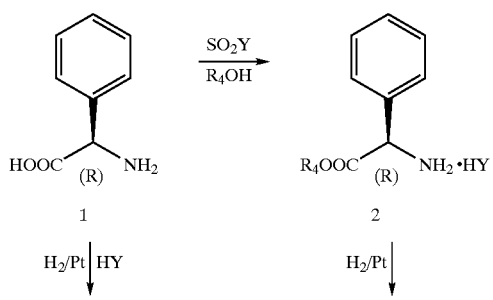

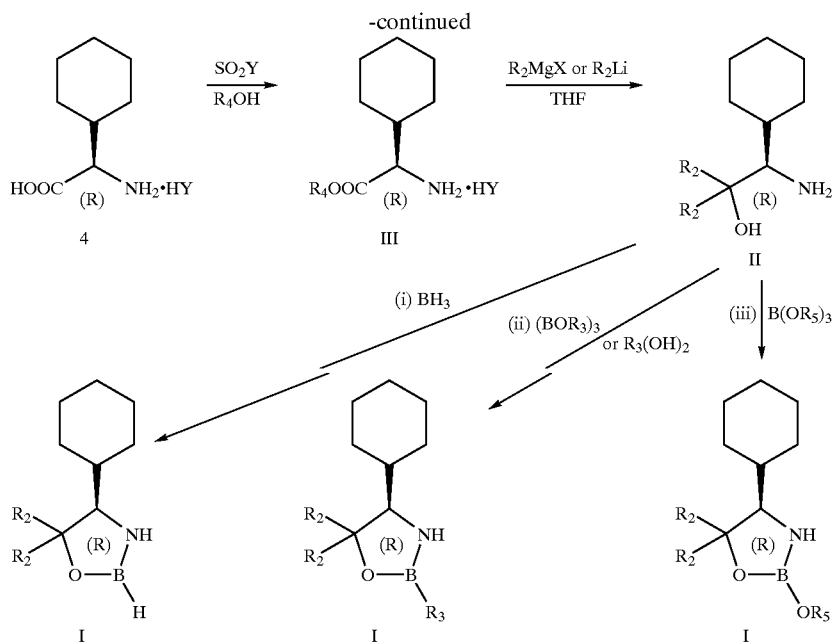

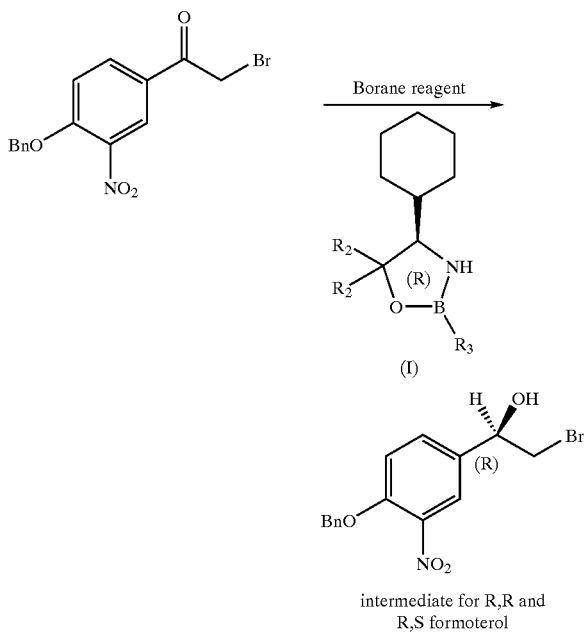

The (R)- and (S)-cyclohexylglycine acid addition salts (compounds of formula 4) and the (R)- and (S)-cyclohexylglycine lower alkyl (e.g., 1 to 8 carbon atoms) ester acid addition salts (compounds of formula III) are known in the art (see e.g., Annalen der Chemie, 523, p. 199 (1936)) or can be prepared by procedures well-known in the art, such as by catalytic hydrogenation of (R)- and (S)-phenylglycine (compounds of formula 1) and (R)- and (S)-phenylglycine lower alkyl ester acid addition salts (compounds of formula 2), respectively. Typically, the organometallic reagents, $R_2MgX$ (Grignard), for example, phenylmagnesiumchloride and 1-naphthylmagnesium bromide, and $R_2Li$ (organolithium), for example, phenyllithium, are either commercially available or can be prepared by methods known in the art. Generally, the borane, $BH_3$, is delivered in the form of a borane reagent, such as diborane gas or borane complexed with either tetrahydrofuran or dioxane, or is complexed to a sulfide, for example, dimethylsulfide-borane complex or 1,4-oxathiane-borane complex, or is complexed to a bis-sulfide, for example, 1,2-bis-(t-butylthio)ethane-diborane complex or 1,2-bis-(benzylthio)butane-diborane complex. The alkyl, aryl or aralkylboronic acid, $[R_3(OH)_2]$, trialkyl, triarylborate or triaralkyl borate, $[B(OR_5)_3]$, and trialkyl, triaryl or triaralkyl boroxine, $[(BOR_3)_3]$, reagents are also either commercially available or can be prepared by methods known in the art.

The inventive compounds of formula I are useful as chiral accessories. Chiral alcohols are advantageously prepared by reacting a borane reagent with a prochiral ketone in the presence of the inventive chiral accessories as defined by formula I. These chiral accessories advantageously serve as enantioselective catalysts for the borane reduction of prochiral ketones to chiral alcohols. The compounds of formula II of the invention are useful as precursors for preparing the compounds of formula I. Some useful chiral intermediates and chiral compounds that are prepared with the aid of the chiral accessories of the invention and some representative inventive processes are shown below. Other useful intermediates and compounds will be evident to those skilled in the art.

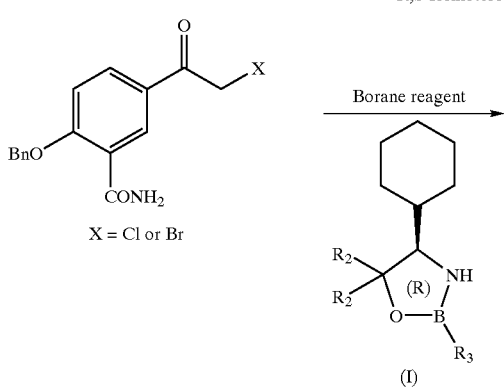

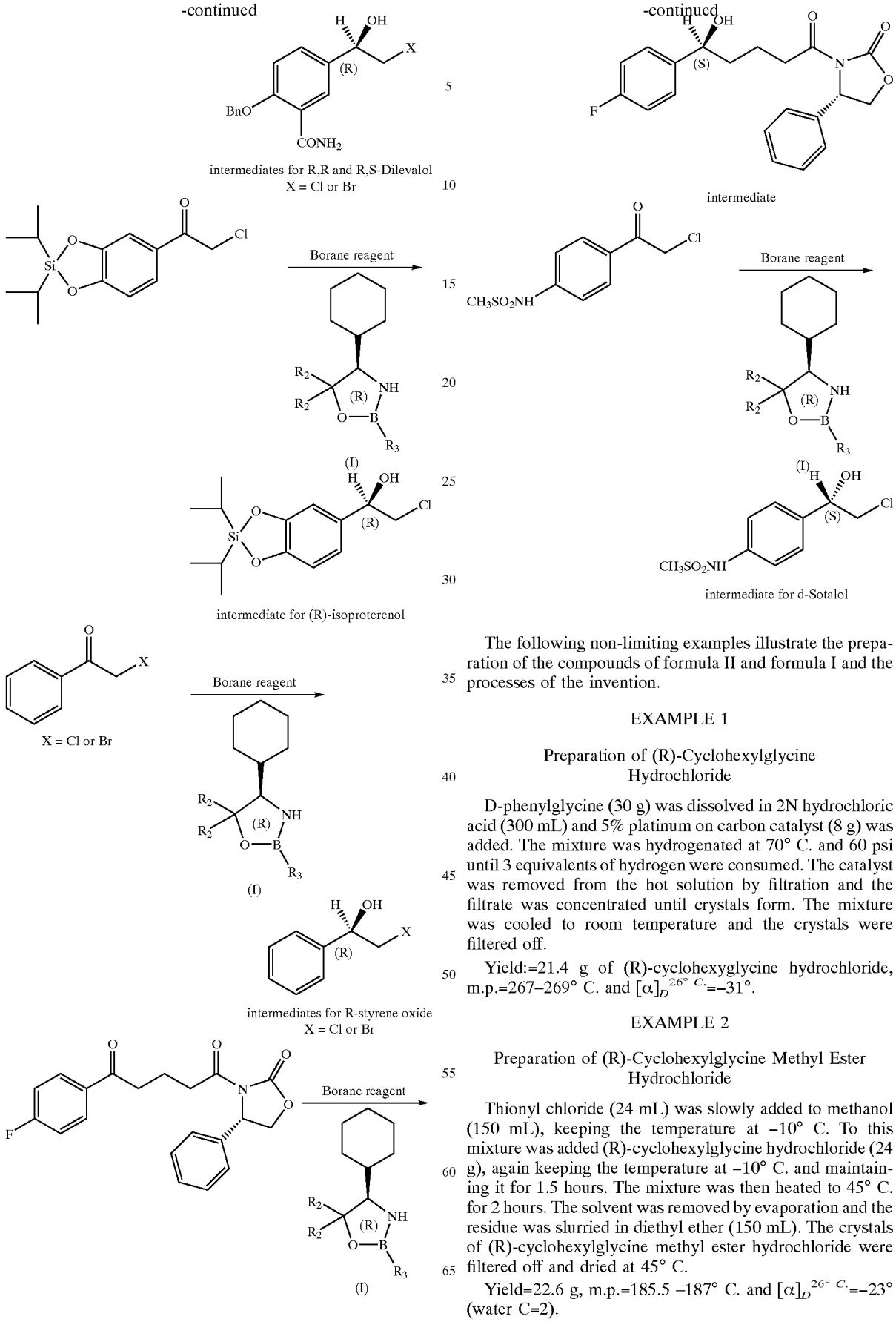

The following non-limiting examples illustrate the preparation of the compounds of formula II and formula I and the processes of the invention.

EXAMPLE 1

Preparation of (R)-Cyclohexylglycine Hydrochloride

D-phenylglycine (30 g) was dissolved in 2N hydrochloric acid (300 mL) and 5% platinum on carbon catalyst (8 g) was added. The mixture was hydrogenated at 70° C. and 60 psi until 3 equivalents of hydrogen were consumed. The catalyst was removed from the hot solution by filtration and the filtrate was concentrated until crystals form. The mixture was cooled to room temperature and the crystals were filtered off.

Yield:=21.4 g of (R)-cyclohexyglycine hydrochloride, m.p.=267–269° C. and $[\alpha]_D^{26°\ C.}=-31°$.

EXAMPLE 2

Preparation of (R)-Cyclohexylglycine Methyl Ester Hydrochloride

Thionyl chloride (24 mL) was slowly added to methanol (150 mL), keeping the temperature at −10° C. To this mixture was added (R)-cyclohexylglycine hydrochloride (24 g), again keeping the temperature at −10° C. and maintaining it for 1.5 hours. The mixture was then heated to 45° C. for 2 hours. The solvent was removed by evaporation and the residue was slurried in diethyl ether (150 mL). The crystals of (R)-cyclohexylglycine methyl ester hydrochloride were filtered off and dried at 45° C.

Yield=22.6 g, m.p.=185.5 –187° C. and $[\alpha]_D^{26°\ C.}=-23°$ (water C=2).

EXAMPLE 3

Preparation of (R)-Cyclohexylglycine Methyl Ester Hydrochloride

Platinum oxide catalyst (78.02%, 3.5 g) was added to a solution of (R)-phenylglycine methyl ester hydrochloride (140 g, 0.694 mole) in methanol (1 L) and the mixture was stirred under an atmosphere of hydrogen at 55 psi for 18 hours. The catalyst was removed by filtration and the methanol solution was concentrated under vacuum to give a solid residue. Diethyl ether (400 mL) was added to this residue and the product was filtered off from the resulting slurry. The (R)-cyclohexylglycine methyl ester hydrochloride was dried under vacuum at 45° C.

Yield=137.5 g, m.p.=182–184° C. and $[\alpha]D^{20° C.}$=–33.4° (13.62 mg/mL MeOH $^1$H NMR (DMSO): δ 0.94–1.76 (10H, m, —CH$_2$—);δ 1.84 (1H, m, —CH—); δ 3.74 (3H, s, —OCH$_3$); δ 3.81 (1H, d, —CH—N); δ 8.61 (3H, s, —NH$_3$).

EXAMPLE 4

Preparation of (R)-2-Amino-2-cyclohexyl-1,1-diphenylethanol

To a solution of phenylmagnesium bromide (3M in diethylether, 200 mL) was added dry tetrahydrofuran (300 mL) and the mixture was cooled to 0° C. (R)-cyclohexylglycine methyl ester hydrochloride (20.77 g) was added in portions keeping the temperature at about 0° C. The reaction mixture was warmed to room temperature and stirred for 16 hours. Ice and 2N hydrochloric acid (280 mL) were added to the reaction followed by ammonium hydroxide (30 mL) to pH=9. The resulting precipitate of magnesium salts was removed by filtration and washed with ethyl acetate. The filtrate was separated into two layers and the aqueous layer was extracted with ethyl acetate (4×150 mL). The extracts were combined with the original organic layer and concentrated under vacuum to give a solid residue product. Recrystallization of the residue from ethyl acetate gave (R)-2-amino-2-cyclohexyl-1,1-diphenylethanol.

Yield=11.33 g, m.p.=181–182° C. and $[\alpha]_D^{20° C.}$=+114.2° (10.07 mg/mL, CHCl$_3$). $^1$H NMR (CDCl$_3$): δ 0.89–1.68 (10H, m, —CH$_2$—); δ 1.95 (1H, m, —CH—); δ 3.75 (1H, d, —CH—N); δ 7.16–7.61 (10H, m, Ph). HR-MS (M+H) calculated for C$_{20}$H$_{25}$NO was 296.2014, and observed was 296.2015. Enantiomeric excess; 99.7% (R), determined by HPLC using a Chiralcel OD-R 25 cm×4.6 mm column with acetonitrile/75 mM aqueous sodium perchlorate 4:6 mobile phase at 1 ml/min at 25° C. Detection with UV at 210 nm.

EXAMPLE 5

Preparation of (S)-Cyclohexylglycine Methyl Ester Hydrochloride

Platinum oxide catalyst (78.02%, 1.5 g) was added to a solution of (S)-phenylglycine methyl ester hydrochloride (60 g, 0.297 mole) in methanol (425 mL) and the mixture was stirred under an atmosphere of hydrogen at 60 psi for 16 hours. The catalyst was removed by filtration and the methanol solution was concentrated under vacuum to provide a solid residue. Diethyl ether (400 mL) was added to this residue and the product was filtered off from the resulting slurry. The (S)-cyclohexylglycine methyl ester hydrochloride was dried under vacuum at 45° C.

Yield=58.7 g, m.p.=183–185° C. and $[\alpha]_D^{20° C.}$=+33.2° (14.8 mg/mL MeOH). $^1$H NMR (DMSO); δ 0.94–1.76 (10H, m, —CH$_2$—);δ 1.84 (1H, m, —CH—); δ 3.74 (3H, s, —OCH$_3$); δ 3.81 (1H, d, —CH—N); δ 8.61 (3H, s, —NH$_3$).

EXAMPLE 6

Preparation of (S)-2-Amino-2-cyclohexyl-1,1-diphenylethanol

To a solution of phenylmagnesium bromide (3M in diethylether, 100 mL) was added dry tetrahydrofuran (150 mL) and the mixture was cooled to 5° C. (S)-cyclohexylglycine methyl ester hydrochloride (10.35 g, 0.3 mole) was added in portions keeping the temperature at about 5° C. The reaction mixture was warmed to 45° C. for one hour and then stirred for about 16 hours at room temperature. Ice and 2N hydrochloric acid (100 mL) was added to the reaction, followed by ammonium hydroxide (30 mL) to provide a pH=9. The resulting precipitate of magnesium salts was removed by filtration and washed with ethyl acetate. The filtrate and washings were separated into two layers and the aqueous layer was extracted with ethyl acetate (4×75 mL). The extracts were combined with the original organic layer and concentrated under vacuum to give a solid residue product. Recrystallization of the residue from ethyl acetate gave (S)-2-amino-2-cyclohexyl-1,1-diphenylethanol. The enantiomeric excess of 98.9% (S) was determined by HPLC using a Chiralcel OD-R 25 cm×4.6 mm column with acetonitrile/75 mM aqueous sodium perchlorate 4:6 mobile phase at 1 ml/min at 25° C. Detection with UV was observed at 210 nm.

Yield=6.5 g, m.p.=181–182° C. and $[\alpha]_D^{20° C.}$=–124.1° (13.06 mg/mL CHCl$_3$). $^1$H NMR (CDCl$_3$): δ 0.89–1.68 (10H, m, —CH$_2$—); δ 1.95 (1H, m, —CH—); δ 3.75 (1H, d, —CH—N); δ 7.16–7.61 (10H, m, Ph).

EXAMPLE 7

Preparation of (S)-2-Amino-2-cyclohexyl-1,1-bis-(4-methoxyphenyl)ethanol

A solution of 4-methoxyphenylmagnesium bromide (21.13g, 0.1 mol) in tetrahydrofuran (200 mL) was cooled to between 0 and 5° C. (S)-cyclohexylglycine methyl ester hydrochloride (3.45 g, 0.0166 mol) was added in portions keeping the temperature below 5° C. The reaction mixture was warmed to 45° C. for 2 hours, then cooled to room temperature and stirred for 16 hours at this temperature. The mixture was cooled again to between 0 and 5° C. and 3N hydrochloric acid (20 mL) was added to the reaction mixture keeping the temperature below 20° C. Ammonium hydroxide solution was added to bring the pH to 9. The resulting precipitate of magnesium salts was removed by filtration and washed with ethyl acetate. The filtrate and washings were separated into two layers and the aqueous layer was extracted with ethyl acetate (2×20 mL). The extracts were combined with the original organic layer and concentrated under vacuum to provide a product in the form of a solid residue. Chromatography of the residue on silica gel eluting with a methylene chloride/ethyl acetate gradient gave 2.45 g of product. Crystallization from ethyl acetate gave (S)-2-amino-2-cyclohexyl-1,1-bis-(4-methoxyphenyl)ethanol.

Yield=2.45 g, m.p.=146–147° C. and $[\alpha]_D^{20° C.}$=–112.9° (10 mg/ml, CHCl$_3$). Mass analysis calculated for C$_{22}$H$_{29}$NO$_3$: was C, 74.33%; H, 8.22% and N, 3.94%. Actual mass found was C, 74.40%; H, 8.22% and N, 3.85%. $^1$H NMR (DMSO-d$_6$); δ 0.75–1.61 (12H, m, —CH$_2$— and NH$_2$); δ 1.86 (1H, bd, —CH—); δ 3.45 (1H, d, —CH—N); δ 3.68 (6H, s, —OCH$_3$); δ 5.11 (1H, s, —OH); δ 6.78 (2H, d, J=9 Hz, Ar); δ 6.80 (2H, d, J=9Hz, Ar); δ 7.32 (2H, d, J=9 Hz, Ar); δ 7.41 (2H, d, J=9 Hz, Ar). HR-MS calculated for C$_{22}$H$_{30}$NO$_3$ was 356.2226, while actual found was 356.2231.

EXAMPLE 8

Preparation of (R)-2-Amino-2-cyclohexyl-1,1-bis-(2-naphthyl)ethanol

Magnesium turnings (1.66 g, 68 mmol) and dry tetrahydrofuran (45 mL) were added to a flask, which was then flushed with nitrogen. A solution of 2-bromonaphthalene (11.8 g, 57 mmol) in dry tetrahydrofuran (10 mL) was then added slowly with gentle warming. When the addition was complete the reaction was refluxed for 30 minutes and then cooled to 0° C. Tetrahydrofuran (10 mL) was added followed by (R)-cyclohexylglycine methyl ester hydrochloride (3.16 g, 15.2 mmol) in portions, keeping the temperature at about 0° C. The reaction mixture was then warmed to 25° C. and stirred for 16 hours. The reaction was cooled with an ice batch, and quenched by adding ice and 2N hydrochloric acid (60 mL). Ammonium hydroxide (6 mL) was added to the mixture to pH=9. The resulting precipitate of magnesium salts was removed by filtration and washed with ethyl acetate. The filtrate and washings were separated into two layers and the aqueous layer extracted three times with ethyl acetate. The extracts were combined with the original organic layer and concentrated under vacuum to give the crude product as a solid residue, which was purified by column chromatography on silica gel, eluting with a hexane/ethyl acetate gradient. The fractions containing the pure product were combined and concentrated to a residue, which was crystallized from ethyl acetate to give (R)-2-amino-2-cyclohexyl-1,1-bis-(2-naphthyl)ethanol.

m.p.=205–206° C. and $[\alpha]_D^{20\ °C}$=+248° (10.4 mg/mL CHCl$_3$). $^1$H NMR (CDCl$_3$); δ 0.84–1.61 (12H, m, —CH$_2$—, NH$_2$); δ 2.05 (1H, br s, —CH—); δ 4.02 (1H, d, J=1.5 Hz, —CHN); δ 7.38–7.51 (5H, m, Ar); δ 7.68–7.75 (5H, m, Ar); δ 7.81–7.87 (12H, m, Ar); δ 8.09 (2H, s, Ar). $^{13}$C NMR (CDCl$_3$); δ 26.136; δ 26.304; δ 26.771; δ 26.847; δ 33.131; δ 38.423; δ 60.213; δ 80.231; δ 123.670; δ 124.105; δ 124.251; δ 125.348; δ 125.568; δ 125.790; δ 125.833; δ 126.032; δ 127.414; δ 127.567; δ 128.195; δ 128.252; δ 128.321; δ 132.107; δ 132.217; δ 133.100; δ 133.259; δ 142.044; δ145.193. HR-MS calculated for C$_{28}$H$_{30}$NO was 396.2327, while actual found was 396.2332.

EXAMPLE 9

Preparation of (S)-2-Amino-2-cyclohexyl-1,1-dibenzylethanol

To a solution of benzylmagnesium chloride (2M in tetrahydrofuran, 75 mL) was added dry tetrahydrofuran (75 mL) and the reaction mixture was cooled to 5° C. (S)-cyclohexylglycine methyl ester hydrochloride (5.715 g, 0.15 mole) was added in portions, keeping the temperature at about 5° C. The reaction mixture was warmed to 45° C. for one hour and then stirred for 16 hours at room temperature. Ice and 2N hydrochloric acid (500 mL) were added to the reaction, followed by ammonium hydroxide (30 mL) to pH=9. The resulting precipitate of magnesium salts was removed by filtration and washed with ethyl acetate. The filtrate and washings were separated into two layers and the aqueous layer was extracted with ethyl acetate (2×35 mL). The extracts were combined with the original organic layer and concentrated under vacuum to give the product as a solid residue. Recrystallization of the residue from hexane gave (S)-2-amino-2-cyclohexyl-1,1-dibenzylethanol.

Yield=4.3 g, m.p.=80–81° C. and $[\alpha]_D^{20\ °C}$=−11.2° (7 mg/mL CHCl$_3$). Mass calculated for C$_{22}$H$_{29}$NO was C, 81.69%; H, 9.04% and N, 4.33%, while actual found was C, 81.22%; H, 8.96% and N, 4.32. $^1$H NMR (DMSO-d$_6$); δ 0.98–1.74 (10H, m, —CH$_2$—); δ 1.80 (1H, d, —CH—); δ 2.65 (2H, q, —CH$_2$Ph); δ 2.70 (2H, q, CH$_2$Ph); δ 3.32 (1H, bs, —CH—N); 64.53 (1H, bs, —OH); δ 7.08–7.46 (10H, m, Ph).

EXAMPLE 10

Preparation of (R)-4-Cyclohexyl-5,5-diphenyl-1,3,2-oxazaborolidine (R)-2-amino-2-cyclohexyl-1,1-diphenylethanol (2.95 g, 10 mmole) was added to dry tetrahydrofuran (19 mL) under a nitrogen atmosphere and the solution was cooled to 0° C. Borane-tetrahydrofuran complex (1M solution in tetrahydrofuran 11 mL) was added. The reaction mixture was kept at room temperature for 2 hours, then diluted with tetrahydrofuran to generate a stock solution of (R)-4-cyclohexyl-5,5-diphenyl-1,3,2-oxazaborolidine (3.07 g) in tetrahydrofuran (30 mL).

EXAMPLE 11

Preparation of (R)-4-Cyclohexyl-5,5-diphenyl-1,3,2-oxazaborolidine (R)-2-amino-2-cyclohexyl-1,1-diphenylethanol (2.95 g, 10 mmole) was added to dry tetrahydrofuran (20 mL) under a nitrogen atmosphere and the solution was cooled to 0° C. Borane-dimethylsulfide complex (1.0 mL, 10 mmole) was added. The reaction mixture was kept at room temperature for 2 hours, then diluted with dry tetrahydrofuran to generate a 0.1 M stock solution of (R)-4-cyclohexyl-5,5-diphenyl-1,3,2-oxazaborolidine (3.07 g in tetrahydrofuran 100 mL).

EXAMPLE 12

Preparation of (R)-4-Cyclohexyl-5,5-diphenyl-2-methyl-1,3,2-oxazaborolidine (R)-2-amino-2-cyclohexyl-1,1-diphenylethanol (2.95 g, 10 mmole) and toluene (60 mL) were charged to a 100 mL single neck flask fitted with a Dean and Stark trap, which was then flushed with nitrogen. The mixture was concentrated by distillation at atmospheric pressure to a volume of 30 mL. Toluene (30 mL) was then added and the mixture was concentrated again by distillation to 30 mL. Toluene (30 mL) was again added and the mixture was concentrated again by distillation to 30 mL. The reaction mixture was cooled to room temperature, trimethylboroxine (0.94 mL, 6.7 mmol) was added and the reaction mixture was stirred at room temperature for 16 hours. Toluene (20 mL) was added and 30 mL of solvent was distilled out. More toluene (30 mL) was added and 30 mL more of the solvent was distilled out. Once again, more toluene (30 mL) was added and then all the solvent was removed by distillation to give (R)-4-cyclohexyl-5,5-diphenyl-2-methyl- 1,3,2-oxazaborolidine.

Yield=3.19 g. $^1$H NMR (CDCl$_3$); -); δ 0.42 (3H, s, —BCH$_3$—); δ 0.76–1.62 (10H, m, —CH$_2$—); δ 1.74 (1H, m, —CH—); δ 3.50 (1H, bs, —NH—); δ 4.14 (1H, d, —CH—N); δ 7.23–7.66 (10H, m, Ph).

The solid product produced above was dissolved in dry tetrahydrofuran to produce 30 mL of a 0.33 M stock solution of (R)-4-cyclohexyl-5,5-diphenyl-2-methyl-1,3,2-oxazaborolidine.

EXAMPLE 13

Preparation of (R)-4-Cyclohexyl-5,5-diphenyl-2-methoxy-1,3,2-oxazaborolidine

A solution of (R)-2-amino-2-cyclohexyl-1,1-diphenylethanol, (2.95 g, 10 mmole) in toluene (34 mL) was distilled to remove (10 mL) of solvent. Additional toluene (17 mL) was added and a further 17 mL of solvent was distilled out. An additional 58 mL of toluene was added and a further 17 mL of solvent was distilled out. A further 17 mL of toluene was added followed by the addition of trimethylboroxine (0.93 mL, 6.68 mmole) at room temperature. The reaction mixture was kept at room temperature for 30 minutes and concentrated to a volume of 10 mL. Toluene (17 mL) was again added and a further 17 mL of distillate was distilled out. Additional toluene (17 mL) was added and the distillation was continued at atmospheric pressure until no more distillate was removed. Dry tetrahydrofuran was added to the residue to give a stock solution of the product (R)-4-cyclohexyl-5,5-diphenyl-2-methoxy-1,3,2-oxazaborolidine (3.2 g) in tetrahydrofuran (30 mL).

EXAMPLE 14

Chiral Reduction of Bromoacetophenone with Borane and (R)-4-Cyclohexyl-5,5-diphenyl-1,3,2-oxazaborolidine (R)-2-amino-2-cyclohexyl-1,1-diphenylethanol (59 mg, 0.2 mmol), dry tetrahydrofuran (2 mL) and borane dimethylsulfide complex (100 µL, 1.0 mmol) were added to a dry flask under an atmosphere of nitrogen. The reaction mixture was stirred at room temperature for 1.5 hr to form (R)-4-cyclohexyl-5,5-diphenyl-1,3,2-oxazaborolidine. A solution of bromoacetophenone (199 mg, 1.0 mmol) in dry tetrahydrofuran (4 mL) was added to the borane/(R)-4-cyclohexyl-5,5-diphenyl-1,3,2-oxazaborolidine complex at the rate of 9 mL/hr by means of a syringe pump. The resulting mixture was stirred at room temperature for an additional 1.5 hr. Methanol was added to quench the reaction and then the solvent was removed by evaporation. The resulting residue was chromatographed on silica gel (hexane/ethyl acetate, 25:1) and combination of the like fractions, followed by removal of the solvent gave (R)-2-bromo-1-phenylethanol (170 mg, 97.9% ee). The enantiomeric excess was measured by HPLC (Chiralcel OD-H column, mobile phase, hexane/2-propanol 9:1, flow rate=0.7 mL/min).

$^1$H NMR (CDCl$_3$); δ 2.53 (1H, bs, —OH); δ 3.61 (2H, m, —CH$_2$Br); δ 4.89 (1H, dd, —CH—); δ 7.29–7.42 (5H, m, —Ph).

EXAMPLE 15

Chiral Reduction of Bromoacetophenone with Borane and (R)-4-Cyclohexyl-5,5-diphenyl-2-methoxy-1,3,2-oxazaborolidine (R)-2-amino-2-cyclohexyl-1,1-diphenylethanol (59 mg, 0.2 mmol), dry tetrahydrofuran (2 mL) and trimethylboroxine (27.2 µL, 0.24 mmol) were added to a dry flask under an atmosphere of nitrogen, then stirred for 1.5 hr to form a solution of (R)-4-cyclohexyl-5,5-diphenyl-2-methoxy-1,3,2-oxazaborolidine. Borane dimethylsulfide complex (100 µL, 1.0 mmol) was added and the reaction stirred for 30 minutes. Then, a solution of bromoacetophenone (199 mg, 1.0 mmol) in dry tetrahydrofuran (4 mL) was added at the rate of 9 mL/hr by means of a syringe pump. After 1.5 hr, methanol was added to quench the reaction and then, the solvent was removed by evaporation. The resulting residue was chromatographed on silica gel (hexane/ethyl acetate 20:1) and combination of the like fractions, followed by removal of the solvent gave (R)-2-bromo-1-phenylethanol (130 mg, 98.7% ee). The enantiomeric excess was measured by HPLC (Chiralcel OD-H column, mobile phase, hexane/2-propanol 9:1, flow rate=0.7 mL/min).

EXAMPLE 16

Chiral Reduction of Bromoacetophenone with Borane and (R)-4-Cyclohexyl-5,5-diphenyl-2-methyl-1,3,2-oxazaborolidine A 0.25 M tetrahydrofuran solution of (R)-4-cyclohexyl-5,5-diphenyl-2-methyl-1,3,2-oxazaborolidine (0.4 mL) (prepared as in example 12) was added to a dry flask containing borane dimethylsulfide complex (0.05 mL, 0.5 mmol) under nitrogen. The mixture was stirred at room temperature for I hour and then, a solution of bromoacetophenone (99.5 mg, 0.5 mmol) in dry tetrahydrofuran (3 mL) was added to the borane/(R)-4-cyclohexyl-5,5-diphenyl-2-methyl-1,3,2-oxazaborolidine complex over 20 minutes via a syringe pump. The reaction was stirred at room temperature for 2 hours. Methanol was added to quench the reaction and then the solvents were removed by evaporation. The residue obtained was dissolved in ethyl acetate, washed with 1M hydrochloric acid and filtered through a silica gel plug. The filtrate was concentrated to provide (R)-2-bromo-1-phenylethanol. The enantiomeric excess=96.2% and was measured by HPLC (Chiralcel OD-H column, mobile phase, hexane/isopropyl alcohol 9:1, flow rate=0.6 mL/min).

EXAMPLE 17

Chiral Reduction of Bromoacetophenone with Borane and (R)-4-Cyclohexyl-5,5-bis-(2-napthyl)-2-methoxy-1,3,2-oxazaborolidine (R)-2-amino-2-cyclohexyl-1,1-bis(2-naphthyl)ethanol (79.1 mg, 0.2 mmol) and dry tetrahydrofuran (2 mL) and trimethylboroxine (27.2 µL, 0.24 mmol) were added to a dry flask under an atmosphere of nitrogen, then stirred for 1 hour to form a solution of (R)-4-cyclohexyl-5,5-bis(2-naphthyl)-2-methoxy-1,3,2-oxazaborolidine. Borane dimethylsulfide complex (100 µL, 1.0 mmol) was added and the reaction was stirred for 30 minutes. Then, a solution of bromoacetophenone (199 mg, 1.0 mmol) in dry tetrahydrofuran (3 mL) was added at the rate of 9 mL/hr by means of a syringe pump. After 2 hours, methanol was added to quench the reaction, followed by 0.5 N ethanolic HCl (0.4 mL). The solvent was removed by evaporation under vacuum and the resulting residue was chromatographed on silica gel (hexane/ethyl acetate 25:2). Combination of the like fractions, followed by removal of the solvent gave (R)-2-bromo-1-phenylethanol (130 mg, 93% yield, 98.3% ee). The enantiomeric excess was measured by HPLC (Chiralcel OD-H column, mobile phase, hexane/2-propanol 9:1, flow rate=0.7 mL/min).

EXAMPLE 18

Chiral Reduction of Bromoacetophenone with Borane and (S)-4-Cyclohexyl-5,5-bis-(4-methoxy)phenyl-1,3,2-oxazaborolidine (S)-2-amino-2-cyclohexyl-1,1-bis-(4-methoxyphenyl)ethanol (71.2 mg, 0.2 mmol), dry tetrahydrofuran (2 mL) and borane dimethylsulfide complex (1 00 µL, 1.0 mmol) were added to a dry flask under at atmosphere of nitrogen. The mixture was stirred at room temperature for 1.5 hours to form (R)-4-cyclohexyl-5,5-bis-(4-methoxy)phenyl-1,3,2-oxazaborolidine. A solution of bromoacetophenone (199 mg, 1.0 mmol) in dry tetrahydrofuran (4 mL) was added to the borane/(R)-4-cyclohexyl-5,5-bis-(4-methoxy)phenyl-1,3,2-oxazaborolidine complex at the rate of 9 mL/hr by means of a syringe pump. The resulting mixture was stirred at room temperature for an additional 1.5 hours. Methanol was added to quench the reaction and then the solvent was removed by evaporation. The resulting residue was chromatographed on silica gel (hexane/ethyl acetate, 25:1) and combination of the like fractions followed by removal of the solvent gave (S)-2-bromo-1-phenylethanol (170 mg, 96.6% ee). The enantiomeric excess was measured by HPLC (Chiralcel OD-H column, mobile phase, hexane/2-propanol 9:1, flow rate=0.7 mL/min).

EXAMPLE 19

Chiral Reduction of (4-Chloroacetyl) methanesulfonanilide with Borane and (R)-4-cyclohexyl-5,5-diphenyl-1,3,2-oxazaborolidine In dry equipment under nitrogen, (R)-2-amino-2-cyclohexyl-1,1-diphenylethanol (29.5 mg, 0.1 mmole), dry tetrahydrofuran (8 mL) and borane/dimethylsulfide complex (50 µL) were added at room temperature. The mixture was stirred for 2 hr to form a solution of (R)-4-cyclohexyl-5,5-diphenyl-1,3,2-oxazaborolidine. A solution of (4-chloroacetyl)-methanesulfonanilide (123.9 mg, 0.5 mmol) in dry tetrahydrofuran (4 mL) was then added at the rate of 9 mL/min by means of a syringe pump. The reaction mixture was stirred overnight and then quenched by the addition of methanol. The reaction mixture was then concentrated to a solid residue, which was then dissolved in ethyl acetate and washed with 2N hydrochloric acid. The ethyl acetate layer was separated, dried over magnesium sulfate and concentrated to give (R)-4-(1-hydroxy-2-chloroethyl)methanesulfonanilide. The enantiomer ratio was 97.5:2.5 (R:S), as measured by chiral HPLC (Chiralcel OD-H column, mobile phase, hexane/ethyl acetate (7:3, flow rate=0.7 mL/min).

$^1$H NMR (CDCl$_3$); δ 2.71 (1H, d, —OH); δ 2.95 (3H, s, —CH$_3$); δ 3.61 (2H, m, —CH$_2$Cl); δ 4.82 (1H, d, —CH—); δ 6,74 (1H, s, —NH); δ 7.16 (2H, d, —ArH); δ 7.33 (2H, d, —ArH);

EXAMPLE 20

Chiral Reduction of (4-Chloroacetyl) methanesulfonanilide with Borane and (R)-4-Cyclohexyl-2-methoxy-5,5-diphenyl-1,3,2-oxazaborolidine Dry (R)-2-amino-2-cyclohexyl-1,1-diphenylethanol (147.7 g, 0.5 mmol), dry tetrahydrofuran (2.5 mL) and trimethylborate (68 µL) were added to a dry flask and stirred at room temperature to produce a solution of (R)-4-cyclohexyl-2-methoxy-5,5-diphenyl-1,3,2-oxazaborolidine. 0.5 mL (0.1 mmol) of this solution was added to a borane/dimethylsulfide complex (50 µL, 0.5 mmol) in a dry flask and a solution of (4-chloroacetyl)methane-sulfonanilide (124 mg, 0.5 mmol) in dry tetrahydrofuran (3 mL) was added over 20 minutes via a syringe pump. The reaction was stirred for a further 2 hours, at which time thin layer chromatography (silica gel, hexane/ethyl acetate 1:1) showed that the reduction was complete. The reaction was then quenched by the addition of methanol and concentrated to a solid residue, which was dissolved in ethyl acetate and washed with 2N hydrochloric acid. The ethyl acetate layer was separated, dried over magnesium sulfate and concentrated to give (R)-4-(1-hydroxy-2-chloroethyl) methanesulfonanilide. The enantiomeric excess=94.3% (R), as measured by chiral HPLC (Chiralcel OD-H column, mobile phase, hexane/ethyl acetate (7:3, flow rate=0.7 mL/min).

EXAMPLE 21

Chiral Reduction of 3,5-(Bistrifluoromethyl) acetophenone with Borane and (R)-4-Cyclohexyl-5, 5-diphenyl-2-methoxy-1,3,2-oxazaborolidine (R)-2-amino-2-cyclohexyl-1,1-diphenylethanol (59 mg, 0.2 mmol), dry tetrahydrofuran (2 mL) and trimethylborate (27.2 µL, 0.24 mmol) were added to a dry flask and stirred under an atmosphere of nitrogen for 1.5 hours. Borane dimethylsulfide complex (100 µL, 1.0 mmol) was added and the reaction mixture was stirred at room temperature for a further 30 minutes. A solution of 3,5-(bistrifluoromethyl) acetophenone (180 µL, 1.0 mmol) in tetrahydrofuran (3 mL) was added by means of a syringe pump at a rate of 9 mL/min and the reaction then stirred for a further 1.5 hours. Thin layer chromatography (silica gel/hexane/ethyl acetate 4:1) showed no starting material. The reaction was quenched by an addition of methanol. The solvent was evaporated under vacuum and the residue was dissolved in ethyl acetate and washed 3 times with 1N HCl. The ethyl acetate solution was dried over magnesium sulfate, filtered through a plug of silica gel and then concentrated to give (S)-1-[3,5-(bistrifluoromethyl)phenylethanol with an ee of 92.6%. The enantiomer ratio was determined by HPLC using a Chiralcel OD 25 cm×4.6mm column with hexane/2-propanol (97:3) mobile phase at 0.7 mL/min at 25° C. Detection with UV was at 254 nm.

EXAMPLE 22

Chiral Reduction of 3,5-(Bistrifluoromethyl) acetophenone with Borane and (S)-4-Cyclohexyl-5, 5-bis-(4-methoxyphenyl)-2-methoxy-1,3,2-oxazaborolidine (S)-2-amino-2-cyclohexyl-1,1-bis-(4-methoxyphenyl) ethanol (71.1 mg, 0.2 mmol), dry tetrahydrofuran (2 mL) and trimethylborate (27.2 µL, 0.24mmol) were added to a dry flask and stirred under an atmosphere of nitrogen for 1.5 hours to form a solution of (S)-4-cyclohexyl-5,5-bis-(4-methoxyphenyl)-2-methoxy-1,3,2-oxazaborolidine. Borane dimethylsulfide complex (100 µL, 1.0 mmol) was added to this solution and the mixture was stirred at room temperature for a further 30 minutes. A solution of 3,5-(bistrifluoromethyl)-acetophenone (180 µL, 1.0 mmol) in tetrahydrofuran (3 mL) was added by means of a syringe pump at a rate of 9 mL/min and the reaction then stirred for a further 1.5 hours. Thin layer chromatography (silica gelhexane/ethyl acetate 4:1) showed no starting material. The reaction was quenched by addition of methanol. The solvent was evaporated under vacuum and the residue was dissolved in ethyl acetate and washed 3 times with 1N HCl. The ethyl acetate solution was dried over magnesium sulfate, filtered through a plug of silica gel and concentrated to give (R)-1-[3,5-(bistrifluoromethyl)phenylethanol. The enantiomer ratio was determined by HPLC using a Chiralcel OD 25 cm×4.6 mm column with hexane/2-propanol (97: 3) mobile phase at 0.7 mL/min at 25° C. Detection with UV was at 254 nm.

$^1$H NMR (CDCl$_3$); δ 1.56 (3H, d, CH$_3$—); δ 1.99 (1H, brs, —OH); δ 5.07 (1H, q, —CH—); δ 7.80 (1H, s, H$_{Ar}$); δ 7.86 (2H, s, H$_{Ar}$) with an ee of 93.3%.

EXAMPLE 23

Chiral Reduction of 1-Tetralone with Borane and (R)-4-Cyclohexyl-5,5-diphenyl-2-methoxy-1,3,2-oxazaborolidine (R)-2-amino-2-cyclohexyl-1,1-diphenylethanol (59 mg, 0.2 mmol), dry tetrahydrofuran (2 mL) and trimethylborate (27.2 μL, 0.24 mmol) were added to a dry flask and stirred under an atmosphere of nitrogen for 1.5 hours to form a solution of (R)-4-cyclohexyl-5,5-diphenyl-2-methoxy-1,3,2-oxazaborolidine. To this solution was added borane dimethylsulfide complex (100 μL, 1.0 mmol) and the mixture was stirred at room temperature for a further 30 minutes. A solution of 1-tetralone (133 μL, 1.0 mmol) in tetrahydrofuran (5 mL) was added by means of a syringe pump at a rate of 16 mL/min and the reaction was then stirred for a further 1 hour. Thin layer chromatography (silica gel/hexane/ethyl acetate 4:1) showed no starting material. The reaction was quenched by addition of methanol. The solvent was evaporated under vacuum and the residue was dissolved in ethyl acetate and washed 3 times with 1N HCl. The ethyl acetate solution was dried over magnesium sulfate, filtered through a plug of silica gel and concentrated to give (S)-1-hydroxy-1,2,3,4-tetrahydronaphthalene with an ee of 96.5%. The enantiomer ratio was determined by HPLC using a Chiralcel OB 25 cm×4.6 mm column with hexane/2-propanol (9:1) mobile phase at 0.5 mL/min at 25° C. Detection with UV was at 254 nm.

$^1$H NMR (CDCl$_3$; δ 1.78–2.10 (4H, m, —CH$_2$—); δ 2.81 (2H, m, —CH$_2$—); δ 4.80 (1H, bs, —CH—); δ 7.13 (1H, m, Ar); δ 7.24 (2H, m, Ar); δ 7.45 (1H, m, Ar).

EXAMPLE 24

Chiral Reduction of 2-Phenylmethoxy-5-bromoacetylbenzamide with Borane and (R)-4-Cyclohexyl-5,5-diphenyl-1,3,2-oxazaborolidine To a solution of (R)-2-amino-2-cyclohexyl-1,1-diphenylethanol (184.6 mg, 0.625 mmol) in dry tetrahydrofuran (5 mL), in dry equipment and under nitrogen at room temperature, was added borane/dimethylsulfide complex (125 μL). The mixture was stirred for 1 hour to form a solution of (R)-4-cyclohexyl-5,5-diphenyl-1,3,2-oxazaborolidine. A solution of 2-phenylmethoxy-5-bromoacetylbenzamide (174.1 mg, 0.5 mmol) in dry tetrahydrofuran was added to the borane/(R)-4-cyclohexyl-5,5-diphenyl-1,3,2-oxazaborolidine complex in one portion and stirred for 90 minutes. The reaction mixture was diluted with water and the tetrahydrofuran was removed by distillation under vacuum. Ethyl acetate and 2.1 mL of 9% hydrochloric acid was added to the residue and then the precipitated (R)-2-amino-2-cyclohexyl-1,1-diphenylethanol hydrochloride was filtered off. The phases of the filtrate were separated, followed by extraction of the aqueous phase with ethyl acetate. A combination of the extracts with the original ethyl acetate phase was carried out, followed by a wash with dilute hydrochloric acid and then with brine. The ethyl acetate was concentrated and the (R)-2-phenylmethoxy-5-(1-hydroxy-2-bromoethyl)benzamide was purified by preparative thick layer chromatography. The product was crystallized from ethyl acetate. The enantiomer ratio was determined by HPLC (Chiralcel OD-H column, mobile phase, hexane/ethanol (4:1) flow rate, 0.6 mL/min). UV detection was at 254 nm.

Yield=0.283 g, m.p.=185.5–187° C. and $[\alpha]_D^{26\,°C.}$-17.3° (c=1.025, MeOH). $^1$H NMR (CDCl$_3$); δ 2.80 (2H, m, —OH); δ 3.60 (2H, m, —CH$_2$Br); δ 4.97 (1H, m, —CHO—); δ 5.23 (2H, s, —CH$_2$Ph); δ 5.82 (1H, bs, —NH); δ 7.11 (1H, d, J=10 Hz, ArH$_3$); δ 7.35–7.53 (5H, m, Ph); δ 7.60 (1H, dd, J=2 Hz, 10 Hz, ArH$_4$); δ 7.77 (1H, bs, —NH); δ 8.26 (1H, d, J=2 Hz, ArH$_6$); Enantiomer ratio 95.5:4.5, (R:S).

EXAMPLE 25

Chiral Reduction of (R)-3-[5-(4-Fluorophenyl)-1,5-diketopentyl]-4-phenyl-1,3-oxazolidin-2-one with Borane and (R)-4-Cyclohexyl-5,5-diphenyl-2-methyl-1,3,2-oxazaborolidine A 1 molar solution of (R)-4-cyclohexyl-5,5-diphenyl-2-methyl-1,3,2-oxazaborolidine was prepared. Dry tetrahydrofuran was added to the product to give a stock solution of 3.19 g (R)-4-cyclohexyl-5,5-diphenyl-2-methyl-1,3,2-oxazaborolidine in 10 mL tetrahydrofuran as described in example 13. Borane/dimethylsulfide complex (2.82 mL) and 1 molar solution of (R)-4-cyclohexyl-2-methyl-5,5-diphenyl-1,3,2-oxazaborolidine chiral catalyst in tetrahydrofuran (5.6 mL, 5.6 mmol) were added to a dry 250 mL flask at room temperature. The mixture was stirred for 15 minutes at room temperature. To this mixture was slowly added with agitation a solution of (R)-3-[5-(4-fluorophenyl)-1,5-diketopentyl]-4-phenyl-1,3-oxazolidin-2-one (10 g, 28 mmol) in methylene chloride (50 mL) 43 minutes. The reaction was quenched after 3.5 hours. The diastereomer ratio of 96:4 (S,R:R,R) was determined by HPLC using a Chiralcel OD-H 15 cm×4.6 mm column with hexane/ethanol 7:3 mobile phase at 0.7 mL/min at 25° C. Detection with UV was at 254 nm.

$^1$H NMR (DMSO-d$_6$); δ 1.37–1.68 (4H, m, —CH$_2$—); δ 2.86 (2H, m, —CH$_2$—); δ 4.13 (1H, m, —CH$_2$O—); δ 4.51 (1H, m, —CHO—); δ 4.72 (1H, m, —CH$_2$O—); δ 5.20 (1H, d, —OH); δ 5.45 (1H, m, —CHN—); δ 7.09–7.43 (9H, m, Ar); $^{13}$C NMR (DMSO-d$_6$); δ 20.64; δ 34.92; δ 38.78; δ 57.21; δ 70.43; δ 71.67; δ 114.83; δ 115.04; δ 126.01; δ 127.89; δ 127.97; δ 128.28; δ 129.14; δ 140.35; δ 142.71; δ 154.07; δ 160.15; δ 162.56; δ 172.36.

The above description is not intended to detail all modifications and variations of the invention, which will become apparent to a skilled artisan upon reading the description. It is intended, however, that all obvious modifications and variations be included within the scope of the present invention, which is defined by the following claims.

What is claimed is:

1. A compound having the formula I:

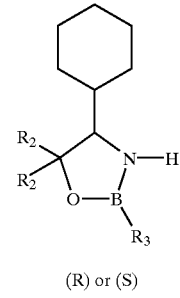

(R) or (S)

where, the two R$_2$ groups are identical and are each a substituted or unsubstituted, aryl, alkyl, cycloalkyl or aralkyl group; and R$_3$ is a hydrogen atom or a substituted or unsubstituted, alkyl, aryl, aralkyl or alkoxy group;

wherein the substituents on the R$_2$ and R$_3$ groups are substantially non-reactive.

2. The compound according to claim 1, where each R$_2$ is a phenyl, 4-methoxyphenyl, 1-naphthyl, 2-naphthyl, 1-naphthylmethyl or 2-naphthylmethyl group.

3. The compound according to claim 2, where R$_3$ is the hydrogen atom or a methyl, butyl, phenyl or methoxy group.

4. The compound according to claim 3, where each R$_2$ is the phenyl group.

5. The compound according to claim 4, where R$_3$ is the hydrogen atom or the methyl group.

6. The compound according to claim 4, where R$_3$ is the methoxy group.

7. The compound according to claim 1, wherein the alkoxy group is unsubstituted and has the formula OR$_5$, where R$_5$ is an unsubstituted alkyl group.

8. A compound having the formula II:

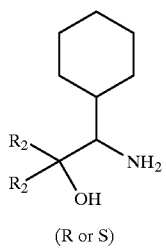

(R or S)

where,
the two $R_2$ groups are identical and are each a substituted or unsubstituted, aryl, alkyl, cycloalkyl or aralkyl group,
wherein the substituents on the two $R_2$ groups are substantially non-reactive.

9. The compound according to claim 8, where each $R_2$ is a phenyl, 4-methoxyphenyl, 1-naphthyl, 2-naphthyl, 1-naphthylmethyl or 2-naphthylmethyl group.

10. The compound according to claim 9, where each $R_2$ is the phenyl group.

11. A process for producing a compound having the formula I:

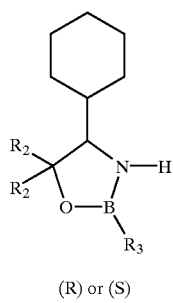

(R) or (S)

where,
the two $R_2$ groups are identical and are each a substituted or unsubstituted, aryl, alkyl, cycloalkyl or aralkyl group; and
$R_3$ is a hydrogen atom or a substituted or unsubstituted, alkyl, aryl, aralkyl or alkoxy group;
wherein the substituents on the $R_2$ and $R_3$ groups are substantially non-reactive, the process comprising:
(a) reacting a (R) or (S) cyclohexylglycine ester hydrochloride or hydrobromide compound having the formula III:

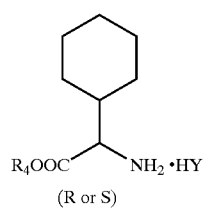

(R or S)

where,
$R_4$ is an alkyl group, and
Y is a chlorine or bromine atom,
with an organometallic reagent having the formula $R_2MgX$ or $R_2Li$, where,
$R_2$ is the same as defined for the compound having the formula I, and
X is a chlorine, bromine or iodine atom,
to form a compound having the formula II:

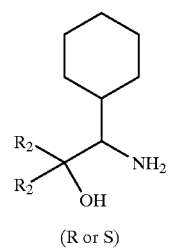

(R or S)

where,
$R_2$ is the same as defined for the compound having the formula I, and
(b) reacting the compound having the formula II formed in step (a) with (i) $BH_3$, (ii) $R_3B(OH)_2$ or $(BOR_3)_3$ or (iii) $B(OR_5)_3$, where $R_3$ is the same as defined for the compound having the formula I and $R_5$ is a substituted or unsubstituted alkyl group,
to form the compound having the formula I.

12. The process according to claim 11, where $R_3$ is an unsubstituted alkoxy group having the formula $OR_5$, where $R_5$ is an unsubstituted alkyl group.

13. A process for asymmetrically reducing a prochiral ketone having the formula IV:

where,
$R_L$ and $R_S$ are different and are each an unsubstituted or substituted, aryl, alkyl, aralkyl or heteroaryl group,
the process comprising reacting the prochiral ketone having the formula IV with borane derived from a borane reagent in the presence of a chiral accessory having the formula I:

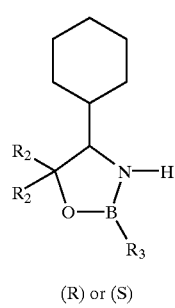

(R) or (S)

where,
the two $R_2$ groups are identical and are each a substituted or unsubstituted, aryl, alkyl, cycloalkyl or aralkyl; and
$R_3$ is a hydrogen atom or a substituted or unsubstituted, alkyl, aryl, aralkyl or alkoxy group,
wherein the substituents on the $R_2$ and $R_3$ groups are substantially non-reactive, to form a chiral secondary alcohol having the formula V:

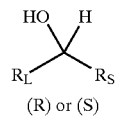

(V)

(R) or (S)

where, $R_L$ and $R_S$ are the same as defined above for the prochiral ketone having the formula IV.

14. The process according to claim 13, wherein $R_3$ is an unsubstituted alkoxy group having the formula $OR_5$, where $R_5$ is an unsubstituted alkyl group.

15. The process according to claim 13, where the two $R_2$ groups are each a substituted or unsubstituted phenyl group and $R_3$ is a hydrogen atom or a substituted or unsubstituted, methyl or methoxy group.

16. The process according to claim 13, where $R_L$ is the unsubstituted or substituted, aryl or heteroaryl group and $R_S$ is the unsubstituted or substituted alkyl group.

17. The process according to claim 16, where the substituted alkyl group is a methyl group substituted with at least one halogen atom.

18. The process according to claim 17, where the at least one halogen atom is chlorine or bromine.

19. The process according to claim 13, where $R_L$ is a phenyl group substituted with a trifluoromethyl group and $R_S$ is a methyl group substituted with a bromine atom, a chlorine atom or a methoxy group.

* * * * *